United States Patent
Stroppiana

(10) Patent No.: US 7,137,285 B2
(45) Date of Patent: Nov. 21, 2006

(54) METHOD AND INSTRUMENT FOR CHARACTERIZING TREADING SURFACES, FOR INSTANCE FOR REALIZING SYNTHETIC TURF SURFACES

(75) Inventor: Fernando Stroppiana, Grinzane Cavour (IT)

(73) Assignee: Mondo S.p.A., Gallo d'Alba (IT)

( * ) Notice: Subject to any disclaimer, the term of this patent is extended or adjusted under 35 U.S.C. 154(b) by 0 days.

(21) Appl. No.: 11/035,418

(22) Filed: Jan. 13, 2005

(65) Prior Publication Data
US 2005/0178184 A1 Aug. 18, 2005

(30) Foreign Application Priority Data
Jan. 16, 2004 (EP) ................. 04425022

(51) Int. Cl.
*G01N 3/00* (2006.01)
(52) U.S. Cl. .............. 73/12.13; 73/78; 73/82; 73/84; 73/12.01; 73/12.05; 73/12.06; 73/12.09
(58) Field of Classification Search ........ 73/12.13, 73/82, 84
See application file for complete search history.

(56) References Cited

U.S. PATENT DOCUMENTS

| 4,337,283 A | 6/1982 | Haas, Jr. .............. 428/17 |
| 5,958,527 A | 9/1999 | Prévost ............... 428/17 |
| 5,976,645 A | 11/1999 | Daluise et al. ........ 428/17 |
| 6,848,293 B1 * | 2/2005 | DeRuiter et al. ...... 73/12.13 |
| 6,925,858 B1 * | 8/2005 | Miles et al. .......... 73/84 |

FOREIGN PATENT DOCUMENTS

| DE | 2 311 654 | 9/1974 |
| EP | 0 377 925 A1 | 7/1990 |
| EP | 1 158 099 A2 | 11/2001 |
| FR | 2 066 356 | 8/1971 |
| GB | 1 524 445 | 9/1978 |
| WO | WO 89/07176 | 8/1989 |

* cited by examiner

*Primary Examiner*—Edward Lefkowitz
*Assistant Examiner*—Freddie Kirkland, III
(74) *Attorney, Agent, or Firm*—Seed IP Law Group PLLC

(57) ABSTRACT

An instrument ("artificial athlete") for characterizing, from the biomechanical standpoint, a treading surface, such as natural grass cover or synthetic grass flooring, is configured for: dropping a weight from a given height on the surface, producing the conversion of kinetic energy of falling of the weight into deformation energy of the surface, the deformation energy being able to be restored by the surface to the weight, bringing about its return/bouncing back upwards; and detecting at least one parameter representing the process of restitution of the deformation energy by the surface to the weight, the parameter identifying the characteristics of tread of the surface.

14 Claims, 5 Drawing Sheets

Fig_1

Fig_2

METHOD AND INSTRUMENT FOR CHARACTERIZING TREADING SURFACES, FOR INSTANCE FOR REALIZING SYNTHETIC TURF SURFACES

BACKGROUND OF THE INVENTION

1. Field of the Invention

The present invention relates to techniques for the characterization of treading surfaces.

2. Description of the Related Art

There exist various known techniques, some of which form the subject of specific standards, designed to enable the characterization of treading surfaces. These techniques have been developed, for example, for identifying, in a reasonably objective way, the characteristics of tread of surfaces such as, for example, floorings made of synthetic material.

These known techniques can be used also for the characterization of surfaces designed for practicing sports activities.

For instance, the standard DIN 18035/7 envisages specific criteria for measuring and calculating a parameter of absorption of energy KA (abbreviation of the German word Kraftabbau), which can be detected using an apparatus known as "artificial athlete of Berlin". The requisites established by the International Federation of Football Association (FIFA) envisage that pitches for playing soccer will have values of KA comprised in the range between 55% and 70%.

The above DIN standard then envisages the possibility of measuring and calculating a parameter of standard deformation using another instrument commonly referred to as "artificial athlete of Stuttgart". The FIFA requisites envisage a range of values between 4 and 8 mm.

Further useful information on the subject can be drawn from the European Standard published at the level of draft in October 2003 as prEN14808.

The "artificial athletes" considered above base their operation on a weight (i.e., a body of predetermined weight) sustained by a base structure resting on the surface to be characterized. The weight is dropped from a given height onto the surface, and associated to the structure is a cup sustained by a spring, which will be struck by the weight as it falls.

In other types of artificial athletes, it is envisaged that the weight will strike the surface to be characterized at the end of its fall: in this case the front face (or impact face) of the weight carries, however, a spring, to which a sensor device for detecting deformation is associated.

In the course of the last few years, synthetic grass floorings of the type described, for example, in EP-A-0 377 925, U.S. Pat. No. 4,337,283, U.S. Pat. No. 5,958,527, U.S. Pat. No. 5,976,645 or EP-A-1 158 099 have found an increasingly wide application.

The solution described in the document cited last enables reproduction in a highly faithful manner of the characteristics of tread and of response to mechanical stresses (bumps, impacts of various nature, etc.) of natural grass cover or turf.

In order to exploit this possibility fully, it is important to identify, in a precise and faithful way—and as objectively as possible—, the characteristics of a given natural grass cover and the characteristics of the synthetic grass flooring (turf) which is desired to be able to reproduce, with the greatest faithfulness possible the characteristics of natural grass cover, this both with specific reference to the biomechanical parameters that essentially determine the interaction of athletes with the surface of the flooring that they use and as regards, for example, the characteristics of bouncing of a ball used for practicing sport on said flooring.

The tests conducted in the course of the last few years demonstrate, however, that the methods and the instruments of characterization of a traditional type, such as those to which reference has been made in the introductory part of the present description, are unable to provide a particularly precise and faithful characterization of a surface, such as, for example, a grass cover, whether natural or synthetic.

BRIEF SUMMARY OF THE INVENTION

One object of the present invention is to provide a structure and method that are able to provide a more reliable characterization of tread surfaces.

According to the present invention, that object is achieved by a method having the characteristics referred to specifically in the ensuing claims. The invention also relates to a corresponding measuring instrument.

Basically, the solution according to the invention is characterized, in the currently preferred embodiment, by the dropping of a weight from a given height onto the surface that is to be characterized, causing the conversion of the kinetic energy of falling of the weight into deformation energy of said surface, the deformation energy being restorable by the surface to the weight. The solution according to the invention hence envisages, in the currently preferred embodiment, detection of at least one parameter representing the process of restitution of the aforesaid deformation energy by the surface to the weight.

In a particularly preferred way, the aforesaid parameter is chosen in the group made up of:
- the peak value of the force of reaction exerted by the surface at the completion of the deformation induced by the falling of said weight; hence, this is, in other words, the initial value of the force with which the surface starts to restore to the weight the deformation energy, i.e., the value of the aforesaid force at the start of the process of restitution of the deformation energy by the surface to the weight;
- the maximum value of deformation of the surface (S) induced by the falling of said weight; also this is, in a symmetrical way, precisely the value of deformation starting from which the surface starts to restore the deformation energy to the weight;
- the interval between the moment when the maximum deformation is reached by the surface as a result of the falling of the weight and the moment in which the weight reaches the maximum value of return (bouncing), induced by the restitution of the deformation energy by the surface to the weight itself;
- the interval between the moment in which the weight hits the surface as a result of the falling of said weight and the aforesaid moment in which the weight reaches the maximum value of return (bouncing), induced by the restitution of the deformation energy to the weight itself by the surface; and/or
- the value of height reached by the weight as a result of the aforesaid phenomenon of return or bouncing, induced by the restitution of the deformation energy to the weight itself by the surface.

The list appearing above is evidently provided by way of example and must not of course be understood in a sense in any way limiting the scope of the invention. However, it is altogether evident that comprised in the framework of the invention are also the solutions based upon combinations and/or processing of the parameters identified above.

Tests so far conducted by the present applicant demonstrate that the last parameter identified above (the value of the height reached by the weight as a result of the phenomenon of return or bouncing) proves particularly significant for the correct characterization of a treading surface, such as grass cover (whether natural or synthetic).

Albeit without wishing to be tied down to any specific theory in this connection, the present applicant has reasons to believe that the marked improvement that can be achieved with respect to the known art is due principally to the fact that, whilst the solutions according to the known art analyze above all the process of deformation of the surface under the effect of the weight that falls thereon, the solution described herein directs attention (also) to what occurs after said process of deformation has taken place, and in particular to the response/reaction offered by the surface in regard to the weight that has fallen thereon.

BRIEF DESCRIPTION OF THE SEVERAL VIEWS OF THE DRAWING(S)

The invention will now be described, purely by way of non-limiting example, with reference to the annexed drawings, in which.

DETAILED DESCRIPTION OF THE INVENTION

First of all, it is recalled that in what follows reference will be made, purely by way of example, to the possible application of the solution described herein for the characterization of treading surfaces consisting of grass cover, whether synthetic or natural. The field of possible application of the invention is not, however, limited to this specific sector: the solution described herein may be used advantageously also for characterizing treading surfaces of a different type, for example floorings for gymnasia, pitches for different games (basket-ball, volley-ball, etc.) and, possibly, also treading surfaces not designed to be used for sporting activities.

"Characterization of treading surfaces" is herein intended to mean the characterization of these surfaces from the biomechanical standpoint, i.e., the identification of the characteristics that determine the behavior of the surface when the latter is subjected to treading.

In the remainder of the present description, general reference will be made to the characterization of a surface S since this is the term used in the sector. In a strict sense, the term "surface" is in itself used to identify an immaterial, i.e., geometrical, quantity, i.e., one virtually without any thickness. In the present context, the term "surface" identifies in actual fact the structure or substrate (in the case of the examples to which extensive reference will be made in what follows, a natural or synthetic grass cover) that defines precisely the surface in question.

Figure 1:
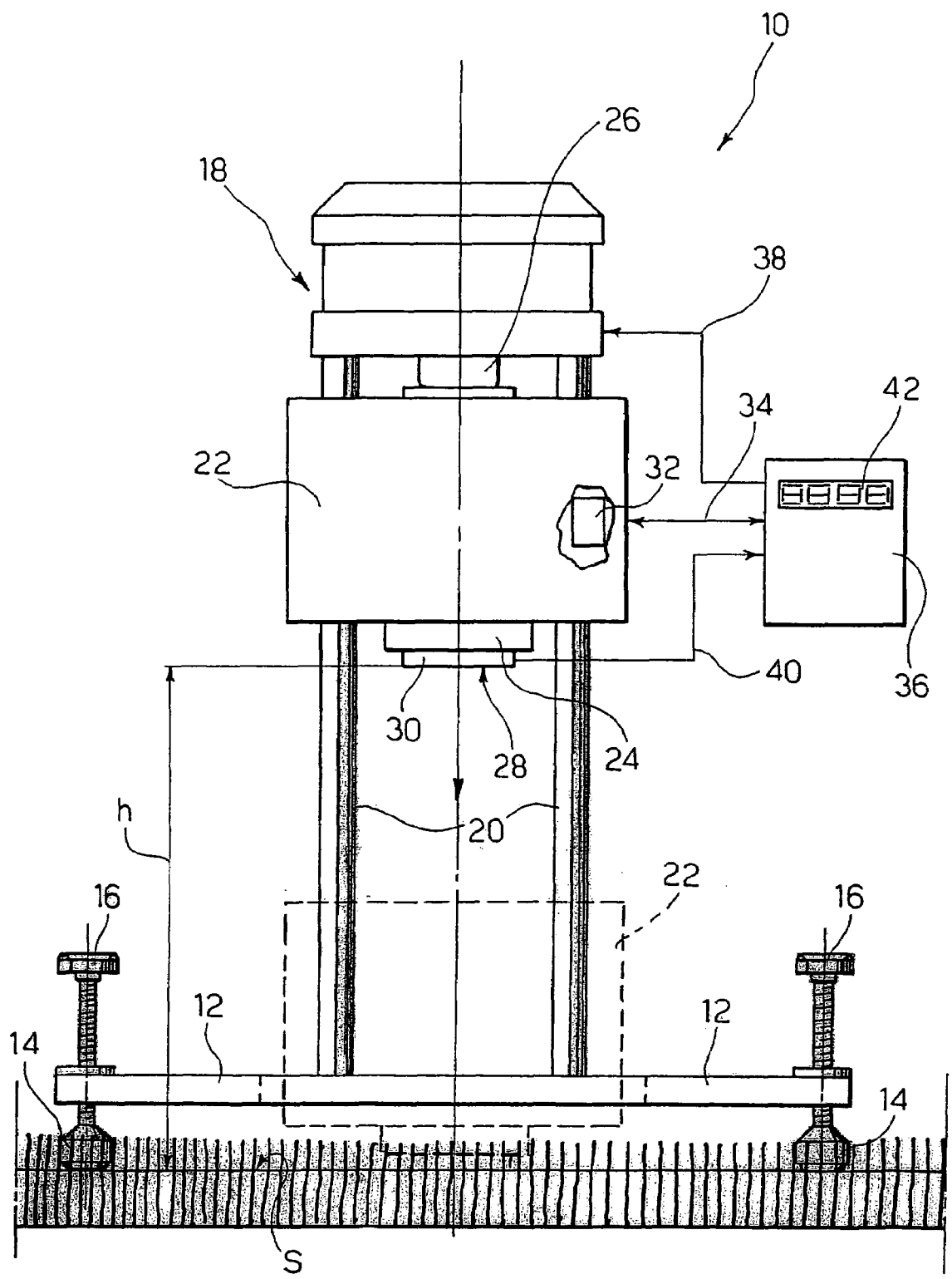
FIG. 1 is an elevational view that illustrates schematically the characteristics of a measuring instrument according to the invention.

In FIG. 1, the reference number 10 indicates, as a whole, an instrument (or "artificial athlete") that can be used for implementation of the solution described herein.

In a way substantially resembling that of other types of artificial athletes already mentioned in the introductory part of the present description, the instrument 10 basically comprises:

a base part comprising a plurality of legs 12 (for example, three legs angularly staggered by 120° with respect to one other), designed to remain firmly on the ground via feet 14; preferably, the feet 14 are provided with elements for micrometric adjustment of height, designated by 16; and a central frame or upright 18 designed to be set in an exactly vertical position by adjustment of the feet 14.

The upright 18 has one or, preferably, a plurality of vertical rods 20, along which there can slide vertically in conditions of low friction a slide 22 carrying a weight 24.

In particular, the slide 22 (and hence the weight 24 carried thereby) is designed to be withheld in a raised position by an electromagnet 26 set in the top part of the upright 18.

The position of retention of the slide 22 by the electromagnet 26 can be selectively adjusted so as to cause the bottom surface of the weight 24 to be at a height h adjusted precisely (for example, within plus or minus five tenths of a millimeter) with respect to the surface S of which it is desired to determine—according to the modalities described in greater detail in what follows—the biomechanical characteristics of tread.

In the following part of the present description, it will be assumed that the surface S is made up of grass cover (either natural or synthetic). The distance h (equal, for example, to 1250 tenths of a millimeter) will then be assumed as determined basically with respect to the surface of the ground from which there emerge the blades of grass.

In order to take into in account the fact that the surface S is in general compliant (also on account of the presence of the filiform formations), adjustment of the height h is made preferably by causing the feet 14 to rest on a plate (template) made of rigid material, for example metal, laid on the ground. Once again in order to take into account the general compliance of the surface S (in which, as described in greater detail in what follows, dropping of the weight 24 can lead to the formation of a more or less marked impression), it is usually envisaged that the operation of setting of the height h will be repeated after each individual test of dropping of the weight 24.

In the case of a synthetic grass flooring of the type like the ones mentioned in the introductory part of the present description, the height h is in general referred to the top level of the infill dispersed between the filiform formations that simulate the sward or turf for the purpose of keeping them in the upright position.

Of course, the value of 1250 tenths of a millimeter indicated above for the height h is to be understood purely for the purpose of providing an example. Similar considerations apply as regards the choice of the weight of the body 24. For example, the tests so far conducted by the present applicant have been carried out with a body having a weight in the region of 11.5 kg. Comprised in said value is also the weight of the slide 22.

At least the top part of the ensemble represented by the slide 22 and the weight 24 (and preferably the entire ensemble) is made of ferromagnetic material.

The electromagnet 26 is designed to withhold the weight 24 initially in the raised position represented by the solid line in FIG. 1. When the electromagnet 26 is deactivated, the weight 24 is released and falls rapidly (in a way that may substantially be viewed as a sort of free fall), starting from the height h and hits, with a front face or surface of impact 28 (i.e., the bottom surface in the condition of normal use of the instrument 10 represented in FIG. 1), the surface S that is to be characterized.

Thus, as will be seen more clearly in what follows, the impact has the characteristics of an at least partially elastic impact and hence leads to a phenomenon of return or bouncing back up of the weight 24.

An important characteristic of the solution described herein lies in the fact that, associated to the front face or surface of impact 28 of the weight 24 is a dynamometric sensor 30 of the type commonly referred to as "load cell".

It is, hence, a sensor designed to detect the force exerted against the front face 28 of the weight 24.

Persons skilled in the sector will moreover appreciate that, albeit preferred, the front arrangement of assembly of the dynamometric sensor 30 is not imperative. The sensor 30 can be mounted also in quite a remote position with respect to the front face 28, albeit retaining the possibility of detecting the intensity of the force applied against said front face during the phenomenon of falling (and bouncing back) of the weight 24 on the surface S.

Unlike what occurs in certain "artificial athletes" according to the known art, in which the aforesaid front face bears a spring associated to which is a deformation sensor, in the case of the device 10 described herein the aforesaid front surface is—substantially—rigid.

The connotation of the front face 28 of the weight 24 as a "substantially rigid" surface has the purpose of taking into account the fact that the dynamometric sensor 30 is made up usually of deformation gauges.

The deformation gauges in question detect the force applied thereto according to the deformation imposed by said force, in particular in the form of a percentage variation in length. For a general illustration of the characteristic of deformation gauges that may be applied in the context of the solution described herein, useful reference may be made to the document "Strain Gauge Measurement—A Tutorial"—Application Note 078—National Instrument Corporation, December 1995 (pages 1 to 11).

The deformations intrinsically linked to the operation of a deformation gauge of said nature are micrometric deformations and, as such, they do not derogate from the characteristic of substantial rigidity of the face of impact 28 of the weight 24: this applies to a particularly evident extent in the case where the dynamometric sensor 30 is mounted in a remote position with respect to the face 28.

Associated to the slide 22 (albeit not explicitly visible in the drawings, but schematically represented by the number 32) are one or more linear-position transducers, which are designed to detect the position reached by the slide 22 (and hence by the weight 24 carried thereby) on the guides 20 of the upright 18. The transducer or the transducers 32 are hence able to detect, with high precision, the distance that separates the front face or surface of impact 28 of the weight 24 from the surface S to be characterized.

The transducers 32 can advantageously consist of contactless linear-position transducers, of the magnetostrictive type. The absence of electrical contact on the slider, eliminates, in transducers of this type, the problems of wear and tear, guaranteeing a practically unlimited duration, at the same time ensuring that the movement of sliding (falling) of the weight 24 along the guides 20 may occur in conditions that may substantially be likened to the conditions of free fall.

Sensors 32 of the type specified above, which present a high performance in terms of linearity, repeatability, resistance to vibrations and to mechanical shocks, are commonly available on the market, and are produced by the firm Gefran S.p.A. of Provaglio d'Iseo (Brescia)—Italy.

The magnetostrictive transducers in question are able to supply, on a respective output line 34, an analog signal directly as a voltage and/or a current, without requiring any electronic treatment of the signal whenever they are interfaced with devices such as a controller or measuring instruments.

The reference number 36 designates a control and processing unit that is advantageously configurable in the form of a personal computer, possibly associated to the device 10 with the provision of an interface (of a known type) for gathering and processing of the measurement data.

The unit 36 controls, via a line 38, the electromagnet 26 (and is thus able to control falling of the weight 24 selectively). It likewise receives, on a line 40, the signal of the dynamometric sensor 30 and hence receives at input a signal representing the force exerted on the front face or surface of impact 28 of the weight 24.

Figure 2:
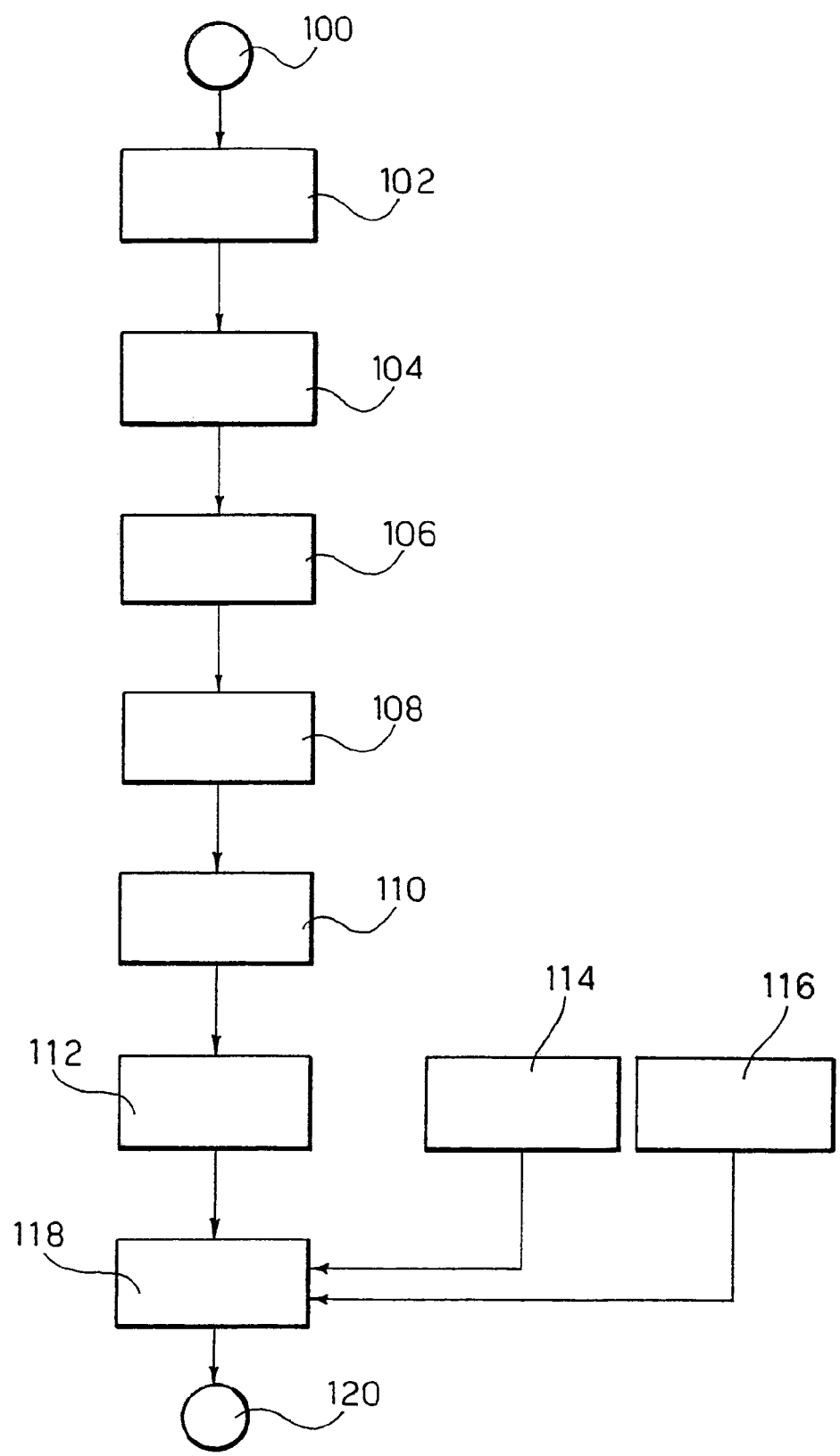
FIG. 2 is a flowchart exemplifying possible criteria of implementation of the solution described herein.

Each individual measurement for the characterization of a surface S using the instrument 10 may advantageously be performed according to the flowchart represented in FIG. 2.

In the flowchart, the step 100 indicates an initial step, in which the instrument 10 is "set" by bringing the slide 22 into a raised position and activating the electromagnet 26 so that the slide 22 and the weight 24 carried thereby are maintained in a raised position, with the front face 28 of the weight 24 located at the distance h (precisely adjustable, for example by operating on the feet 14) from the surface S that is to be characterized.

In a step 102, the control unit 36 controls deactivation of the electromagnet 26, causing the weight 24 to fall vertically along the upright 18 so as to reach gradually the position designated by the dashed line in FIG. 1.

During the movement of falling and in the immediately subsequent steps, the unit 36 records, with a set of operations, represented, as a whole, by step 104, the trend of the output signal of the position sensor or sensors 32 and of the dynamometric sensor 30.

In a preferred way, the operation of detection in question entails sampling of the output signal of the position sensor or sensors 32 and of the dynamometric sensor 30 at a frequency of approximately 20 kHz.

Figure 3:
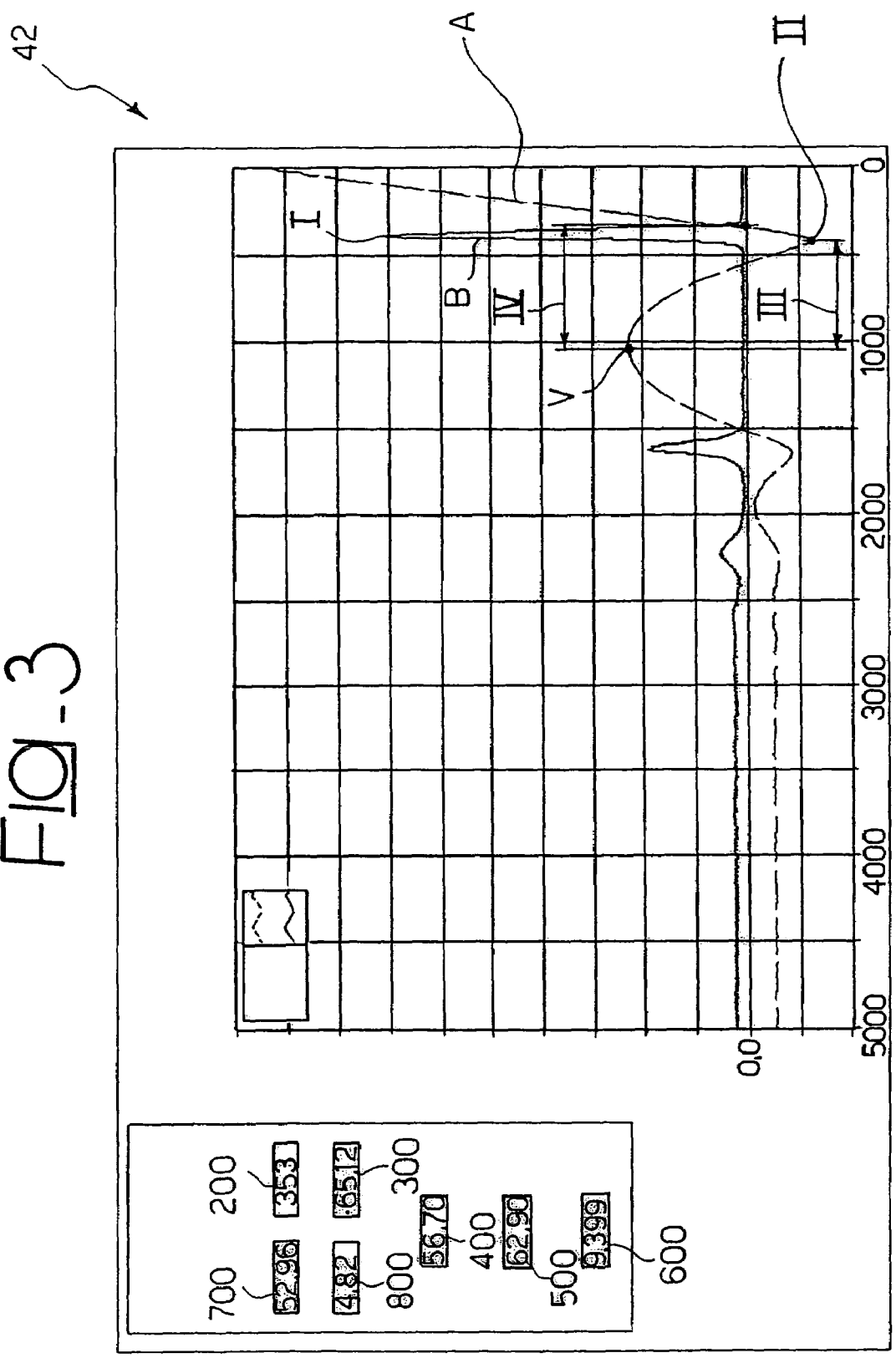
FIGS. 3 to 5 illustrate diagrams that may be obtained with the solution described herein.
Figure 4:
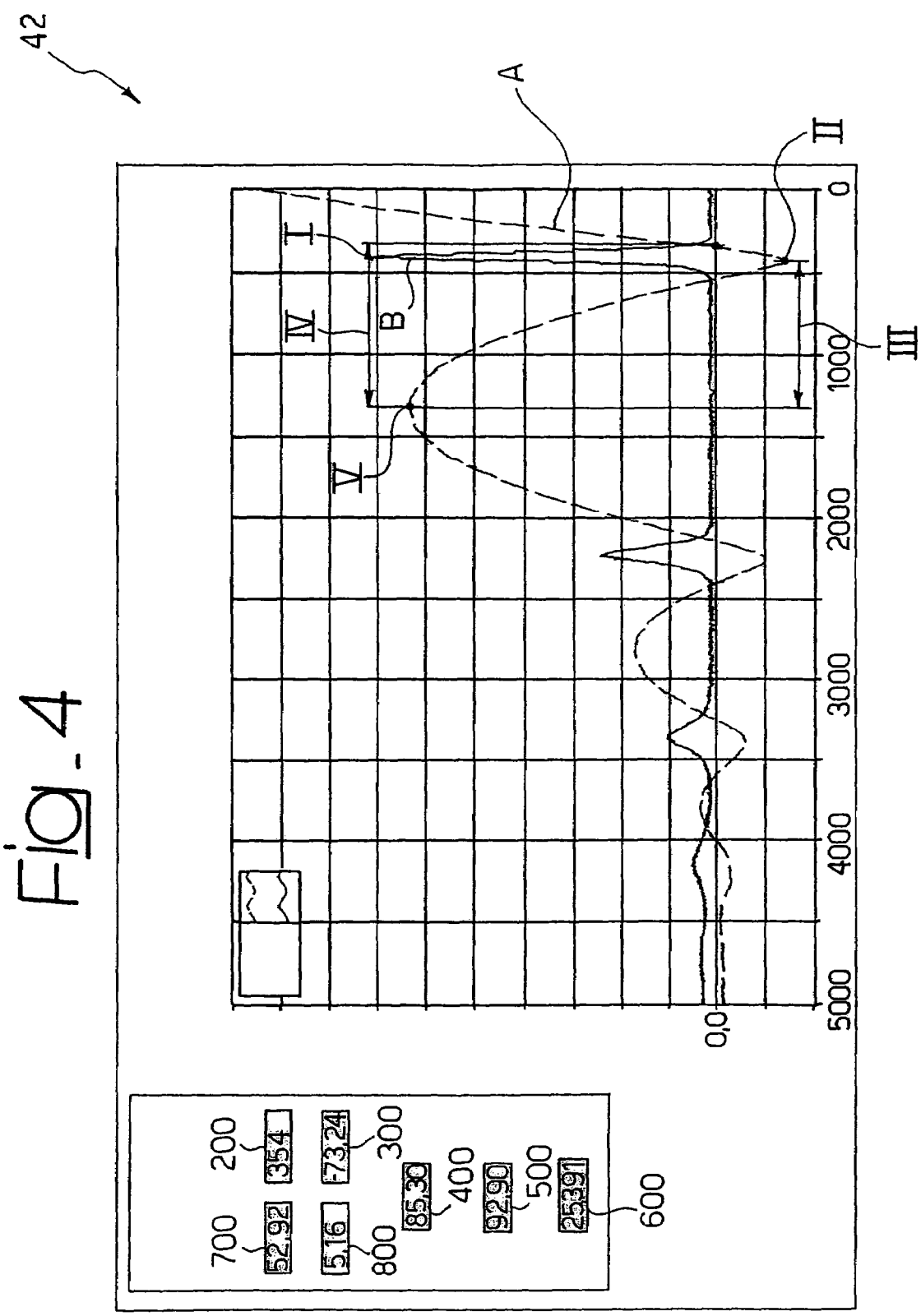
Figure 5:
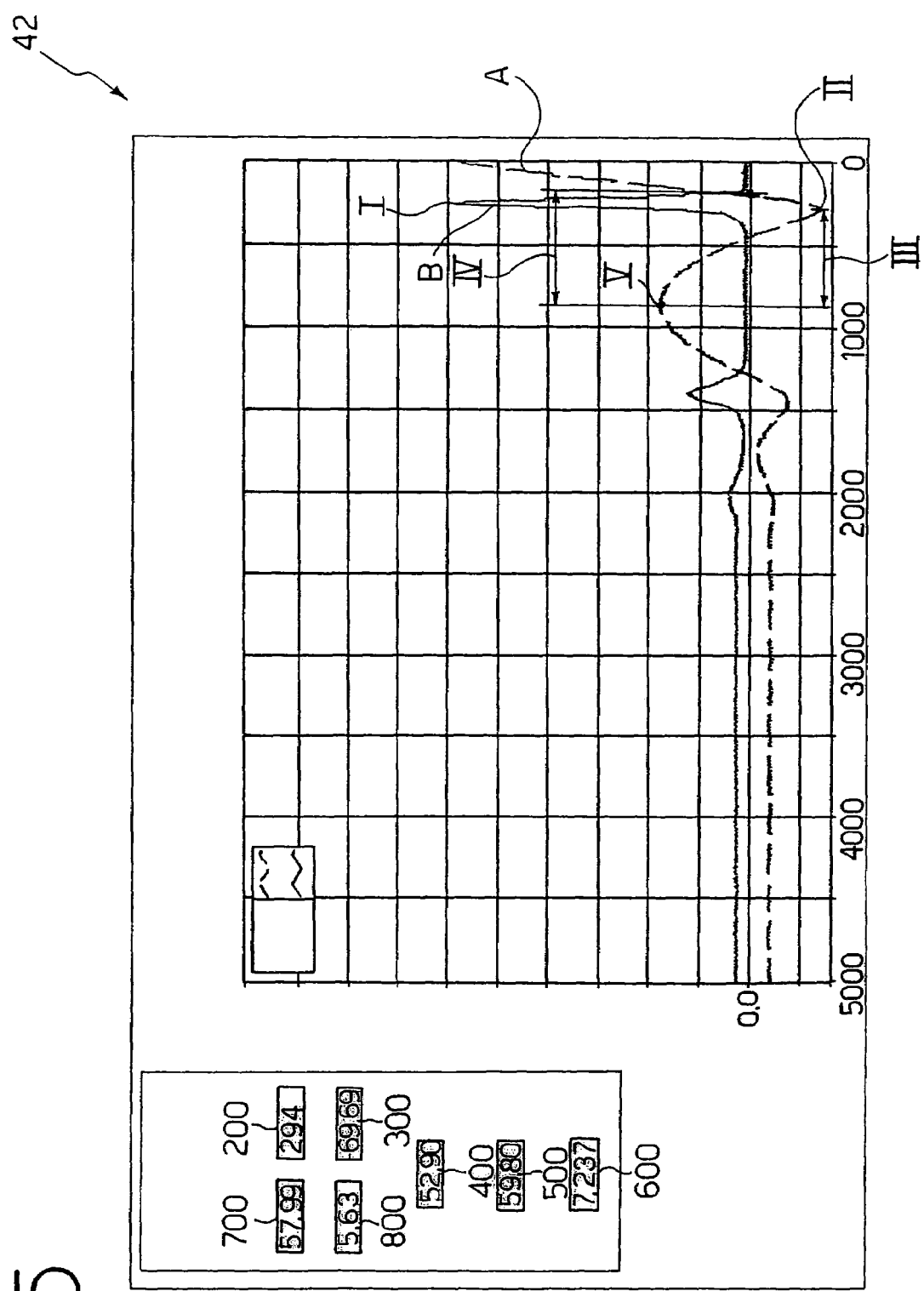

In this way, the unit 36 is able to gather and store signals basically corresponding to the diagrams indicated, respectively, by the curves A and B in the graphs of FIGS. 3, 4 and 5.

In the diagrams in question, the scale of the abscissa is a time scale with orientation from right to left. In other words, the point designated by 0 (on the right) represents the instant in which the electromagnet 26 disengages the slide 22, causing the weight to fall whilst the time scale, measured in milliseconds, represents the time of evolution of the phenomena represented by the curves A and B.

The curve A represents, instant by instant, the vertical position of the front face 28 of the weight 24, measured with respect to the plane of lie of the surface S.

At the instant 0 of the abscissa scale, the corresponding value of height is equal to the value h. In the temporal portion immediately subsequent to disengagement of the slide 22 by the electromagnet 26, the value of said height decreases rapidly as a result of the vertical falling of the weight 24 along the guides 20.

The value of ordinate 0 in the diagrams of FIGS. 3 to 5 corresponds to the condition in which the front face 28 of the weight moves to the position exactly corresponding to the surface S.

With reference to all three diagrams of FIGS. 3 and 5 (and putting off analysis of the differences to a successive step), it may be noted that initially the weight 24 proceeds in its movement of falling, penetrating within the surface S, deforming it.

The movement of penetration proceeds up to the point of minimum of the curves, designated by A in the diagrams.

Starting from this point/moment, the surface S "restores" the deformation energy, displacing once again upwards the weight 24, which returns/bounces back up until it reaches a maximum distance of return/bouncing with respect to the surface S, and then drops back down, penetrating again into the surface S (negative values of the scale of the ordinate of the diagrams of FIGS. 3 to 5) and thus giving rise to new phenomena of bouncing (particularly evident in the curve A of FIG. 4), which are then gradually damped.

For this purpose, the weight 24 usually comes to rest on the surface S in a position in which the front surface 28 is at least slightly below the original level of the surface S; this fact is altogether understandable, since, in the presence of a compliant surface S, the weight 24 tends to form a sort of more or less hollow impression in the surface S.

The curve B of the diagrams corresponds to the output signal of the dynamometric sensor 30 and hence has a pattern coordinated with respect to the pattern of the diagram A.

The force signal B basically presents peaks in the regions of maximum deformation of the surface S and in the immediately subsequent steps, in which the surface (i.e., more correctly, the flooring delimited superficially by said surface) restores the deformation energy accumulated, sending the weight 24 back upwards.

It will be appreciated that the curve B has (in all three of the diagrams of FIGS. 3 to 5) a first very marked peak corresponding to the first phenomenon of return/bouncing and subsequent increasingly less important peaks.

It will also be appreciated, as immediately perceptible, that whilst in the diagrams of FIGS. 3 and 5 the curve B has basically three visible peaks, in the diagram of FIG. 4 the same curve presents, as clearly visible, at least one fourth peak of the force signal.

The steps 106 to 112 of the flowchart of FIG. 2 identify subsequent steps of processing, conducted by the unit 36 (or by the processing module such as a personal computer, to which the latter is connected) on the output signals of the sensors 32 and 30.

In particular, in a step 106, the unit 36 detects the maximum value, designated by I (and normally expressed in kgf), of the force exerted by the weight 24 on the surface S and hence, as evident effect of reaction, by the surface S on the weight 24. This is hence the initial value (maximum) of the force with which the surface S restores to the weight 24 the deformation energy accumulated as a result of the impact of the weight 24 on the surface S.

This value is usually presented on a display screen 42 associated to the unit 36, in particular in a display field designated by 200 (see FIGS. 3 to 5).

The parameter indicated is a biomechanical parameter not envisaged by any standard currently in force at the moment of filing of the present application and is considered as representing the "return" that an athlete who walks or runs on the surface S experiences, following upon each individual impact.

In a step designated by 108, the unit 36 identifies the value of the first minimum, designated by II, of the curve designated by A.

This value of deformation, presented also on the display unit 42 in a field designated by 300, is indicative of the maximum actual deformation of the surface S consequent on impact, measured for example in tenths of a millimeter. It is hence the value of initial deformation, starting from which the surface S restores to the weight 24 the deformation energy accumulated as a result of the impact of the weight 24 on the surface S. It is also in this case a parameter of a biomechanical type, not envisaged by any standard currently in force at the moment of filing of the present application.

In a step designated by 110, the unit 36 determines the duration of the time interval (designated by III) between the point in which the maximum deformation is reached (point referred to previously and designated by II) and the maximum value, which follows immediately thereon, of the curve A, i.e., the moment in which there is the maximum value of height of return or bouncing of the weight 24 upwards with respect to the surface S.

The time of return III, measured usually in thousandths of a second, is basically indicative of the duration of the process with which the surface S restores to the weight 24 the deformation energy accumulated as a result of the impact of the weight 24 on the surface S.

The time of return III is displayed in a field 400 of the display unit 42. Also in this case it is a biomechanical parameter, not envisaged by any standard currently in force at the moment of filing of the present application, which is proportional to the time of reactivity of the surface S.

In a step 112, the unit 36 then detects a value of return time corresponding to the interval designated by IV in the diagrams of FIGS. 3 to 5.

It is basically a parameter akin to the parameter III seen previously, with the difference given by the fact that the time interval in question, designed to be displayed in a field 500 of the display unit 42, is detected not starting from the point of minimum II of the curve A, but rather from its zero value reached at the moment in which the weight 24 hits the surface S.

Also this parameter represents the process with which the surface S restores to the weight 24 the deformation energy accumulated as a result of the impact of the weight 24 on the surface S, but includes within it also a measurement of the duration of the initial process of deformation.

Also in this case, the parameter, expressed in thousandths of a second, is not envisaged by any standard currently in force at the moment of filing of the present application. Also this is proportional to the time of reactivity of the ground.

Finally, in a step designated by 118, the unit 36 detects the ratio between the value of ordinates (designated by V) of the first maximum of the curve A and the height of falling of the weight 24, designated by h.

Also in this case, this is a parameter representing the process whereby the surface S restores to the weight 24 the deformation energy accumulated as a result of the impact of the weight 24 on the surface S. Once again this is a parameter of a biomechanical type not envisaged by any standard currently in force at the moment of the filing of the present application.

The experiences conducted by the present applicant show that it is a particularly significant parameter. The parameter in question, which is usually designed to be presented in a field 600 of the display unit 42 in the form of a percentage value, is proportional to the energy return that the athlete experiences following upon each individual impact.

It will be appreciated, in fact, that the movement of falling (and of subsequent return/bouncing gradually damped) of the weight 24 upwards is based essentially upon a mechanism of bidirectional conversion of potential energy into kinetic energy, and vice versa.

In particular, during the movement of initial falling of the weight 24, the potential energy initially possessed thereby (which is linked to the height h) is converted into kinetic energy, which reaches the maximum value at the moment in which the front face 28 of the weight 24 hits the surface S.

In the immediately subsequent instants, the kinetic energy is transferred to the surface S (or, more correctly, to the flooring of which the latter forms part) in the form of work absorbed and accumulated by the surface S as deformation energy.

The surface S then restores to the weight 24 the deformation energy accumulated, sending it back upwards and transferring then to the weight 24 a kinetic energy which enables it to move again upwards with a movement of return/bouncing. The movement of return upwards involves a (re)transformation of the kinetic energy into potential energy, which reaches a new peak (maximum value) corresponding to the value of ordinate designated by V in the diagrams of FIGS. 3 to 5.

The aforesaid mechanism is repeated of course (in a progressively more damped way) in the successive phenomena of falling/return upwards.

As already mentioned previously, and once again without wishing to be tied down to any specific theory in this connection, the present applicant has reasons to believe that the majority of the techniques of biomechanical characterization of treading surfaces known to the art aim at investigating principally the space-time law of falling of a weight on the surface to be characterized, without giving any particular importance to the identification of the mechanism with which the deformation energy accumulated in the surface is again transferred to the weight bringing about its return upwards, a mechanism which occurs in altogether particular ways, above all in the case where the surface S presents visco-elastic characteristics.

The steps designated by 114 and 116 in the flowchart of FIG. 2 finally indicate the fact that, together with the operations of detection and display described previously, it is possible to detect and display the values of KA and of standard deformation to which reference has been made in the introductory part of the present description. Said parameters can also be deduced from the signals supplied by the sensors with which the device/instrument 10 described herein is equipped, the purpose being to proceed to a display (exemplified by the step 118) of these additional parameters, in respective fields 700 and 800 of the display unit 42.

Passing now to the comparative examination of the diagrams of FIGS. 3 to 5, it is to be noted that the diagram of FIG. 3 relates to a natural grass cover of a commonly used soccer pitch.

The diagram of FIG. 4 relates, instead, to an artificial synthetic flooring made up of synthetic grass filled in with granules of EPDM rubber and sand.

Finally, the diagram of FIG. 5 relates to a synthetic grass flooring produced by the present applicant according to the solution described in EP-A-1 158 099.

Comparison of the diagrams of FIGS. 3 and 5 (and reading of the values appearing in the fields 200 to 600) reveals, in an objective and measurable way, a phenomenon repeatedly encountered by athletes who have experienced and been able to compare both of the types of cover in question. In particular, it may be noted how the curves A and B present, in both cases, a substantial affinity of characteristics, both as regards the absolute values and as regards the time trend.

It may, instead, immediately be appreciated that the curves A and B of FIG. 4 (regarding a synthetic grass flooring/turf filled in with granules of rubber and sand) present an amply different pattern, characterized by an extremely high value of energy return.

In particular, it may be noted that, whilst for the diagrams of FIGS. 3 and 5, the values displayed in the field 600 are respectively 9.399% and 7.237%, the same value is, in the case of FIG. 4, 25.391%, hence approximately three times as high. This corresponds to an extremely high value of energy return, which indicates a synthetic grass flooring that shows a marked character of elasticity, which is harmful for the athlete and such as to give rise to extremely unnatural phenomena of bouncing of a ball used for a sports event.

It may immediately be noted that the values of KA detected in the case of the (natural and synthetic) grass cover of FIGS. 3 and 4 are practically identical (52.96% and 52.92%), whereas in actual fact the two kinds of grass cover in question have altogether different characteristics of behavior. The same considerations apply, to a fair extent, as regards the values displayed in the field designated by 800.

Of course, even though in the currently preferred embodiment of the invention there is envisaged detection and display of all the parameters indicated in the fields 200, 300, 400, 500 and 600, the solution described herein is suited for being implemented by detection of a more restricted group of said parameters.

The tests conducted by the present applicant show that a good characterization of a surface S can be achieved by detecting even just one of said parameters linked to the restitution of the deformation energy by the surface S undergoing testing.

It is deemed that among said parameters, the parameter of energy return (yielded by step 112 and displayed in the field 600 of the display unit) will be particularly interesting and significant, in particular for those applications in which it is desired to achieve a synthetic grass flooring (turf) such as might reproduce in the most faithful way possible the characteristics of a given natural grass cover.

It is known that natural grass cover can present, also in the case of pitches that are quite close to one another, biomechanical characteristics perceived as different by the athletes that use them. Between different pitches available in the same sports facility and/or in the same installation, the athletes can indicate a pitch that is particularly preferred by them.

The solution described herein thus enables "photographing", in an objective and precise way, of the characteristics of one such pitch and their reproduction in the most faithful possible way in a synthetic and artificial flooring, possibly enabling verification with an action of control of an interactive type of the effective correspondence between the characteristics of the synthetic flooring obtained and the characteristics desired. This also applies to the possible evolution of the flooring over time.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Of course, without prejudice to the principle of the invention, the details of construction and the embodiments may vary widely with respect to what is described and illustrated herein, without thereby departing from the scope of the present invention, as defined by the annexed claims.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for characterizing a treading surface, the method comprising the operations of:
   dropping a weight from a given height onto said surface;
   producing the conversion of the kinetic energy of falling of the weight into deformation energy of said surface (S), said deformation energy being able to be restored by said surface to said weight;
   detecting at least one parameter representing the process of restitution of said deformation energy by said surface to said weight, said at least one parameter identifying the characteristics of tread of said surface;
   measuring a bounce height (V) reached by the weight as a result of the aforesaid return upwards induced by the restitution of the weight; and
   determining the deformation energy of the surface from the bounce height.

2. The method according to claim 1, characterized in that said at least one parameter is chosen out of the group comprising:
   the value (I) of the force of reaction exerted by said surface at the start of the process of restitution of said deformation energy by the surface to the weight;
   the value of deformation (II) of said surface at the start of the process of restitution of said deformation energy by the surface to the weight;
   the interval of time (III) between the start of the process of restitution of said deformation energy by the surface to the weight and the moment in which the weight reaches the maximum value of return upwards induced by the restitution to the weight itself of said deformation energy by said surface;
   the interval of time (IV) between the moment in which the weight hits said surface as a result of the falling and the moment in which the weight reaches the maximum value of return upwards induced by the restitution to the weight itself of said deformation energy by said surface; and
   the value of height (V) reached by the weight as a result of the aforesaid return upwards induced by the restitution to the weight itself of said deformation energy by said surface.

3. The method according to claim 1, characterized in that it comprises the operation of detecting the ratio between said value of height (V) of return and said predetermined height (h) of falling of said weight.

4. The method according to claim 1, characterized in that it comprises the operation of displaying said at least one detected parameter.

5. The method according to claim 1, characterized in that said surface is a grass cover or flooring.

6. The method according to claim 5, characterized in that said grass cover or flooring is a natural grass cover.

7. The method according to claim 5, characterized in that said grass cover or flooring is a synthetic grass flooring in the form of a turf.

8. The method for the construction of synthetic grass floorings, characterized in that it comprises the operations of:
   characterizing, using the method according to claim 1, a natural grass cover, by detecting at least one parameter (I to V) in relation to said natural grass cover;
   making a synthetic grass flooring or turf;
   characterizing said synthetic grass flooring using the method according to claim 1, by detecting homologously said at least one parameter (I to V) on said synthetic grass flooring or turf; and
   rendering said synthetic grass flooring or turf similar, from the biomechanical standpoint, to said natural grass cover, causing said at least one parameter (I to V) detected homologously for said synthetic grass flooring or turf to approximate said at least one parameter (I to V) detected for said natural grass cover.

9. An instrument for the characterization of treading surfaces, comprising:
   a structure, which can be positioned on a surface (S) that is to be characterized;
   a weight carried by said structure with the capacity of falling on the surface (S), starting from a given height (h), said weight having a front face, which is substantially rigid and is able to hit said surface as a result of the falling of said weight from said predetermined height (h);
   a dynamometric sensor, which is able to detect the force transferred between said front face of the weight and the surface, generating a respective force signal;
   a position sensor, which is able to detect a vertical position reached by said weight with respect to said structure, generating a respective position signal;
   an element of retention of the weight, which is able to sustain said weight and drop it selectively on said surface from said given height (h), producing the conversion of the kinetic energy of falling of the weight into deformation energy of said surface, said deformation energy restored by said surface to said weight; and
   a processing unit connected to said dynamometric and position sensors, said processing unit configured for detecting, starting from said force and position signals, at least one parameter (I to V) representing the process of restitution of said deformation energy by said surface to said weight, said at least one parameter identifying the characteristics of tread of said surface and detecting a value of height (V) reached by the weight as a result of the aforesaid return upwards induced by the restitution to the weight itself of said deformation energy by said surface.

10. The instrument according to claim 9, characterized in that said processing unit is configured for detecting at least one parameter selected out of the group consisting of:
    the value (I) of the force of reaction exerted by said surface at the start of the process of restitution of said deformation energy by the surface to the weight;
    the value of deformation (II) of said surface at the start of the process of restitution of said deformation energy by the surface to the weight;
    the interval of time (III) between the start of the process of restitution of said deformation energy by the surface to the weight and the moment in which the weight reaches the maximum value of return upwards induced by the restitution to the weight itself of said deformation energy by said surface;
    the interval of time (IV) between the moment in which the weight hits said surface as a result of the falling and the moment in which the weight reaches the maximum value of return upwards induced by the restitution to the weight itself of said deformation energy by said surface; and
    the value of height (V) reached by the weight as a result of the aforesaid return upwards induced by the restitution to the weight itself of said deformation energy by said surface.

11. The instrument of claim 9, comprising a display unit for displaying said at least one detected parameter.

12. An instrument for the characterization of treading surfaces, comprising:
- a structure, which can be positioned on a surface (S) that is to be characterized;
- a weight carried by said structure with the capacity of falling on the surface (S), starting from a given height (h), said weight having a front face, which is substantially rigid and is able to hit said surface as a result of the falling of said weight from said predetermined height (h);
- a dynamometric sensor, which is able to detect the force transferred between said front face of the weight and said surface, generating a respective force signal;
- a position sensor, which is able to detect a vertical position reached by said weight with respect to said structure, generating a respective position signal;
- an element of retention of the weight, which is able to sustain said weight and drop it selectively on said surface from said given height (h), producing the conversion of the kinetic energy of falling of the weight into deformation energy of said surface, said deformation energy restored by said surface to said weight; and
- a processing unit connected to said dynamometric and position sensors, said processing unit configured for detecting, starting from said force and position signals, at least one parameter (I to V) representing the process of restitution of said deformation energy by said surface to said weight, said at least one parameter identifying the characteristics of tread of the surface and detecting the ratio between a value of height (V) of return and said predetermined height (h) of falling of said weight.

13. The instrument of claim 12, wherein the processing unit is configured to detect at least one parameter selected from the group consisting of:
- the value (I) of the force of reaction exerted by the surface at the start of the process of restitution of said deformation energy by the surface to the weight;
- the value of deformation (II) of the surface at the start of the process of restitution of said deformation energy by the surface to the weight;
- the interval of time (III) between the start of the process of restitution of said deformation energy by the surface to the weight and the moment in which the weight reaches the maximum value of return upwards induced by the restitution to the weight itself of said deformation energy by the surface;
- the interval of time (IV) between the moment in which the weight hits the surface as a result of the falling and the moment in which the weight reaches the maximum value of return upwards induced by the restitution to the weight itself of said deformation energy by the surface; and
- the value of height (V) reached by the weight as a result of the aforesaid return upwards induced by the restitution to the weight itself of said deformation energy by the surface.

14. The instrument of claim 12, comprising a display unit for displaying said at least one detected parameter.

* * * * *